(12) United States Patent
Boyce

(10) Patent No.: US 7,452,720 B2
(45) Date of Patent: Nov. 18, 2008

(54) APPARATUS FOR PREPARING A BIOCOMPATIBLE MATRIX

(75) Inventor: Steven T. Boyce, Cincinnati, OH (US)

(73) Assignees: University of Cincinnati, Cincinnati, OH (US); Shriners Hospitals for Children, Tampa, FL (US)

( * ) Notice: Subject to any disclaimer, the term of this patent is extended or adjusted under 35 U.S.C. 154(b) by 325 days.

(21) Appl. No.: 11/142,950

(22) Filed: Jun. 2, 2005

(65) Prior Publication Data

US 2005/0221484 A1     Oct. 6, 2005

Related U.S. Application Data

(62) Division of application No. 10/091,849, filed on Mar. 6, 2002, now Pat. No. 6,905,105.

(51) Int. Cl.
*C12N 5/00*     (2006.01)

(52) U.S. Cl. .................. 435/397; 435/402; 424/424

(58) Field of Classification Search ............... None
See application file for complete search history.

(56) References Cited

U.S. PATENT DOCUMENTS

| | | | |
|---|---|---|---|
| 1,050,145 A | 1/1913 | Korneffel et al. ............ 249/149 |
| 2,367,779 A | 1/1945 | Hull .............................. 18/19 |
| 3,334,383 A | 8/1967 | Irvine .......................... 18/19 |
| 3,816,045 A | 6/1974 | Cawley et al. ............... 425/175 |
| 4,113,225 A | 9/1978 | Corse ........................ 249/169 |
| 4,458,678 A | 7/1984 | Yannas et al. ............... 128/155 |
| 4,817,911 A | 4/1989 | Infanti ......................... 249/82 |
| 4,946,640 A | 8/1990 | Nathoo ....................... 264/316 |
| 4,954,236 A | 9/1990 | Kushner et al. .......... 204/299 R |
| 4,974,809 A | 12/1990 | Lipke et al. ................... 249/82 |
| 5,667,192 A | 9/1997 | Van Doren .................. 249/82 |
| 5,711,172 A | 1/1998 | Boyce ........................ 249/112 |
| 5,976,878 A | 11/1999 | Boyce ........................ 435/366 |
| 6,231,741 B1 | 5/2001 | Tuurenhout et al. ......... 204/618 |
| 6,341,952 B2 | 1/2002 | Gaylo et al. ................... 425/84 |
| 6,905,105 B2 | 6/2005 | Boyce ........................ 249/112 |

FOREIGN PATENT DOCUMENTS

WO     WO 8808305     11/1988

OTHER PUBLICATIONS

European Patent Office, *International Search Report*, PCT/US03/06479, mailed Jul. 23, 2003 (3 pgs.).

*Primary Examiner*—James S Ketter
(74) *Attorney, Agent, or Firm*—Thompson Hine LLP

(57) ABSTRACT

An apparatus and method of using the apparatus to prepare a biocompatible biodegradable matrix capable of supporting cells to form an implantable or engraftable surgical device. A matrix-forming fluid is contained within a chamber defined by top and bottom surfaces of a thermally conductive material and spacers defining the thickness of the matrix. The chamber is then cooled to freeze the solution at a controlled rate, resulting in a matrix with a desired and uniform thickness having symmetric and uniform reticulations. The apparatus and method reproducibly forms such a matrix, which may be populated with cells for transplantation and engraftment into a wound.

19 Claims, 8 Drawing Sheets

APPARATUS FOR PREPARING A BIOCOMPATIBLE MATRIX

RELATED APPLICATIONS

This application is a Divisional of U.S. patent application Ser. No. 10/091,849, filed on Mar. 6, 2002, now U.S. Pat. No. 6,905,105 incorporated by referenced in its entirety herein.

FIELD OF THE INVENTION

The invention is directed generally to an apparatus and method to prepare a biocompatible reticulated matrix that may be used to support cells to form a surgical device such as a cultured skin substitute device.

BACKGROUND

Skin is one of the largest organs in the body and covers substantially the entire body surface. Skin is composed of two main layers: the surface epithelium or epidermis, which contains keratinocytes as one type of epidermal cells, and the subjacent connective tissue layer or dermis, which contains fibroblasts as one type of dermal cells. The functions of skin include protecting an organism from injury and dessication by serving as a barrier to infection, perceiving or detecting environmental stimuli, excreting various substances, regulating body temperature, and helping to maintain water balance. Because of its quantitative and qualitative importance, substantially intact and healthy skin is crucial, not only for the well being of an organism but for its very survival.

The health and integrity of skin may be compromised by congenital or acquired pathological conditions, either acute or chronic, for which normal skin regeneration and repair processes may be inadequate. These conditions include, but are not limited to, burns, wounds, ulcers, infections, and/or congenital abnormalities. Patients who are burned over a large surface area often require immediate and extensive skin replacement. Less life-threatening but chronic skin conditions, as occur in venous stasis ulcers, diabetic ulcers, or decubitus ulcers as three examples, may progress to more severe conditions if left untreated, particularly since patients with these conditions have an underlying pathology. Reduction of morbidity and mortality in such patients depends upon timely and effective restoration of the structure and function of skin.

Skin substitutes derived either ex vivo or in vitro may be used to treat these or other conditions. Desirable skin substitutes are readily available, require a minimum amount of donor skin, are otherwise simple to produce, and are cost-effective to generate and maintain. Several approaches to produce skin substitutes which satisfy some or all of these requirements have been attempted, with varying degrees of success. However, no skin substitute has yet regenerated all of the structures and functions of skin. Rather, all are subsets of uninjured skin. Only a transplant of full thickness skin, which demonstrates scarring during healing, and restores virtually all structures and functions of normal uninjured skin.

Materials have been manufactured for use in permanent skin repair. These materials contain different components replacing or simulating the components and functions of the dermis and/or epidermis. Examples of these materials include EpiCel™, which lacks a dermal component and uses the patient's own cultured keratinocytes; Integra™, which uses a collagen-glycosaminoglycan (GAG) matrix to provide an acellular dermal component and uses a thin epidermal autograft; AlloDerm™, which uses a dermal matrix and a thin epidermal autograft; DermaGraft™, which uses a polyglycolic acid/polylactic acid (PGA/PLA) matrix and allogeneic human fibroblasts for the dermis; Hyaff/LaserSkin™, which uses hyaluran and fibroblasts for the dermis, and hyaluran and the patient's own keratinocytes for the epidermis; and Poly-Active™, which uses polyethylene oxide/polybutylthalate (PEO/PBT) and the patient's own fibroblasts for the dermis, and the patient's cultured keratinocytes for the epidermis.

Materials to either temporarily cover wounds, or to stimulate permanent skin repair processes, included ApliGraft™, which uses collagen gel and allogeneic fibroblasts for the dermis, and cultured allogeneic keratinocytes for the epidermis; Comp Cult Skin™ or OrCel™, which uses collagen and allogeneic fibroblasts for the dermis, and cultured allogeneic keratinocytes for the epidermis; and TransCyte™, which uses allogeneic fibroblasts for the dermis and a synthetic material, BioBrane™, for the epidermis.

While the above materials are useful to varying degrees, each has disadvantages and limitations. Some of the materials are mechanically fragile, making it difficult to perform the required manipulations and transfers of the material in large sections without tearing. Instead, the materials must be used as smaller pieces, which makes coverage of large surface areas technically laborious for the physician and cosmetically undesirable for the patient. The materials are also susceptible to microbial contamination, which is unacceptable for patients who are already at an increased risk for infection due to their compromised condition. The materials show varying rates of engraftment and time to heal, both of which must be considered in balancing the advantage of a particular material over another for a particular patient. For example, a material which is otherwise acceptable but which takes longer to engraft and heal is less desirable, since recovery includes as rapid a return to a normal routine as possible.

Yannas et al. in U.S. Pat. No. 4,458,678 discloses a method for preparing a fibrous lattice and seeding it with viable cells. The lattice is prepared by pouring an aqueous slurry of collagen and glycosaminoglycan into an open metal tray or pan. Use of an open tray results in asymmetric contact of the slurry to ambient conditions; that is, one surface of the slurry is in contact with a surface of the tray or pan ("pan surface"), while another surface of the slurry is in contact with the atmospheric environment ("air surface"). The pan is then placed in contact with a heat sink, such as the refrigerated shelf of a lyophilizer, to initiate freezing of the aqueous slurry from the pan side. Freezing proceeds predominantly in a vectorial direction from the pan surface to the air surface, with heat flowing much more rapidly toward the pan surface than the air surface. Upon freezing, the structure of the lattice is asymmetric with, generally, more frequently distributed reticulations of polymers toward the pan surface than the air surface. After freeze-drying, the resulting lattice is an asymmetric structure, which results in non-uniform ability for cells to penetrate the lattice. Furthermore, the method and apparatus of Yannas limit both the uniformity of thickness, and the minimum thickness that can be obtained consistently and deliberately.

The inventor's own previous composite skin replacement, disclosed in U.S. Pat. No. 5,976,878, which is expressly incorporated by reference herein in its entirety, has been used successfully for permanent skin replacement. It is applied surgically in a single procedure, and contains a layer of cultured epidermal cells, a synthetic dermal membrane component, and a substantially nonporous synthetic lamination layer on one surface of the dermal membrane component. The synthetic dermal membrane component is formed from collagen, or collagen and a mucopolysaccharide compound, and is laminated with the same collagen or collagen and mucopolysaccharide compound-containing solution containing a volatile cryoprotectant. The substantially nonporous lamination layer may be located between the dermal component and the layer of cultured epidermal cells, promoting localization of epidermal cells on the surface of the dermal component and movement of nutrients to the cells of the cellular epidermal component. This composition can also be used to deliver biologically active molecules to the site where it is applied. The apparatus for preparing the synthetic dermal membrane component, used to prepare the composite skin replacement of the '878 patent, is disclosed in U.S. Pat. No. 5,711,172, which is expressly incorporated herein by reference in its entirety.

Desirable features of the above-described composite skin replacement included an increased rate of vascularization of the area covered by the material, decreased microbial contamination, increased nutrient supply, and improved epidermal barrier function, compared to other materials. Areas covered with the composite skin replacement required less time to engraft and heal, and the material was less susceptible to microbial contamination compared to other materials. Other desirable features were that this material was relatively non-fragile and easy to handle, and could be generated relatively rapidly, for example, within the time frame in which a burn patient would require skin grafts. However, while no other alternative material has healed excised, full thickness wounds more rapidly, and with as low an incidence of microbial contamination, limitations still exist. Thus, there remains a need to more closely approach the structural and functional properties of normal uninjured skin.

SUMMARY OF THE INVENTION

The invention is directed to an apparatus for the preparation of a biocompatible, biodegradable, matrix having substantially symmetrical reticulations to support cells inoculated thereon. The cells may be cultured skin cells for formation of an engraftable device for the surgical replacement of skin in burn patients, for example. Basically, a solution of matrix components is cast between top and bottom surfaces (e.g., plates) of a material which facilitates rapid transfer of heat, so that the solution in contact with these surfaces is rapidly and uniformly cooled on both top and bottom surfaces. Once frozen, the solid matrix has substantially symmetric reticulations, which allow uniform cell population and result in an improved device for ingrafting or implanting in a patient. The apparatus and method of using the apparatus results in reproducible matrices each time the apparatus is used, so that reproducible devices are generated.

In one embodiment, the apparatus contains a chamber defined by top and bottom planar surfaces of a heat conductive material, such as a metal. The sides of the chamber are defined by at least one gasket of substantially uniform thickness positioned between the top and bottom surfaces. Closures, such as clips, latches, clamps, etc. hold the planar surfaces together. The assembled apparatus allows indirect contact by a coolant and subsequent freezing of the matrix-forming solution. The chamber may be immersed in the coolant, either vertically or horizontally, as in a coolant bath.

In another embodiment, the apparatus containing the above-described chamber may be further contained within a jacket through which a coolant flows or recirculates. In this embodiment, the apparatus also has top and bottom frames which are affixed to the top and bottom surfaces of the heat conductive material. The top and bottom frames contain one or more ports and channels through which a coolant fluid flows. The embodiment provides a contained apparatus to effect the desired rate of cooling.

In another embodiment, the invention is directed to a method of preparing the matrix using the apparatus. A matrix-forming solution is contained within a chamber and is in contact with a material which allows rapid and substantially uniform removal of heat from the top and bottom surfaces of the solution. Gaskets of a desired thickness separate the top and bottom surfaces and allow control over the thickness of the resulting matrix. Using a coolant that can effect the desired rate of cooling, the solution contained in the chamber is frozen to form a solid matrix. The solid matrix is then dehydrated and crosslinked using physical methods such as freeze-drying and thermal crosslinking, rather than by adding chemical crosslinking compounds, the residue of which may negatively affect the formed matrix and the cells with which it comes in contact. The resulting physically-crosslinked matrix is then sterilized before cells are inoculated. The matrix thus prepared has a thickness and reticulation pattern which facilitates uniform population with cells and results in a device which is readily engrafted or transplanted into a patient.

These and other features of the invention will be further appreciated with reference to the following drawings and detailed description.

DETAILED DESCRIPTION

Figure 1A:
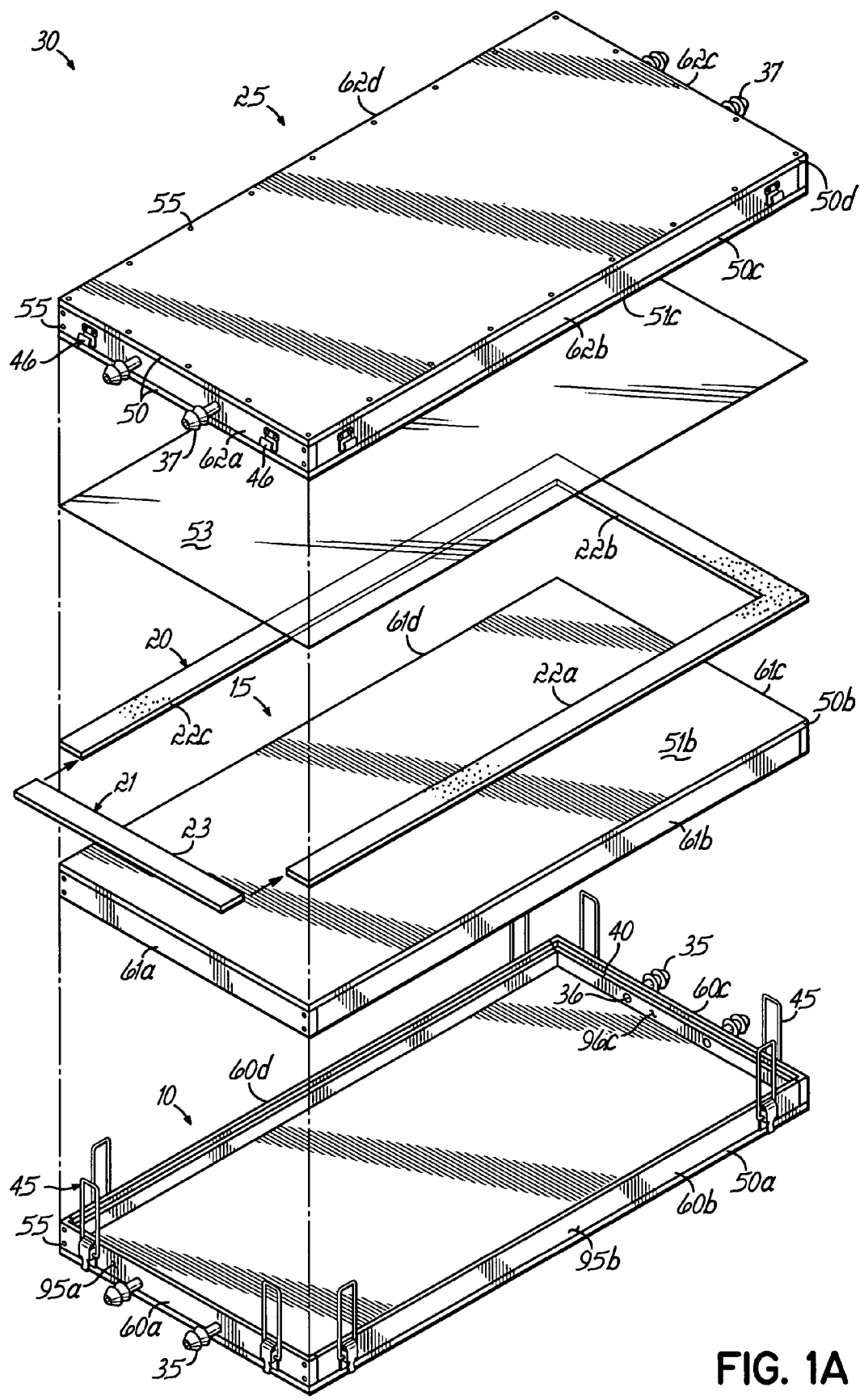
FIG. 1A shows components of one embodiment of a matrix-casting apparatus.

The invention is a method and apparatus to prepare an acellular biocompatible biodegradable matrix having substantially uniform and symmetric reticulations that are formed by freezing an aqueous fluid containing protein, or protein and carbohydrate, at a controlled rate, and subsequent freeze-drying (lyophilization) and a uniform thickness of less than 1 mm. The reticulated matrix is capable of serving as a support or scaffold for cells inoculated thereon. The cells are animal cells, which encompass human cells. In one embodiment, the cells are epidermal and dermal cells, resulting in a cultured skin device as disclosed in co-pending related U.S. patent application Ser. No. 10/092,237, entitled Surgical Device For Skin Therapy or Testing and filed on even date herewith, which is expressly incorporated by reference herein in its entirety. The device prepared using the inventive apparatus facilitates cell attachment to the multiple continuous surfaces of the matrix and maintains a desired thickness. This is in contrast to a matrix with asymmetric reticulations and less uniform thickness that is formed when a fluid containing protein, or protein and carbohydrate, contacts an open tray or pan during matrix formation.

Biological incorporation of a matrix into or overlying a wound depends, in part, upon the ability of non-inflammatory connective tissue cells to migrate into the matrix from the wound bed. Thus, the structural and biochemical characteristics of the matrix must be uniform, and further must be optimized to promote fibrovascular migration. The inventive method and apparatus controls structural characteristics of the matrix, such as its thickness and the uniformity and size of the resulting reticulations, by the symmetric extraction of heat from the matrix-forming fluid and the rigid and co-planar surfaces from which heat is extracted. This results in a matrix with symmetric reticulations and uniform thickness. Other variables that are controlled include the rate of cooling to effect freezing the matrix-containing fluid, the size of the ice crystals formed, the volume of the matrix-forming fluid that is frozen, and the concentration (% wt/vol) of the components in the matrix-forming fluid.

In one embodiment, the invention is an apparatus to prepare a biocompatible degradable reticulated matrix. The apparatus has a closed chamber to contain a matrix-forming fluid, such as a protein containing fluid. The chamber may be defined by six sides, as in a box. In this embodiment, two of the sides are heat conductive (e.g., metal), parallel rectangular plates that are made more rigid by a framework of reinforcing supports outside of the chamber that contains the matrix-forming fluid. The remaining four sides of the chamber may consist of material that acts as a gasket or O-ring, and may be adjusted in thickness to define the thickness of the resulting matrix. In one embodiment, the gasket consists of two pieces of material. One piece has two parallel strips connected at one end by a perpendicular strip (U-shaped) that are located to adjoin three of the four edges of the two plates. The matrix-forming fluid may be introduced into the chamber through the side without a gasket (open side). Subsequently, the second gasket piece is placed between the fourth edges of the two parallel plates as a single strip to contain the matrix-forming solution. In another embodiment, the gasket is a singular, rectangular strip or O-ring adjoining the perimeters of the two parallel plates, and may have ports for introduction of the matrix-forming solution and displacement of air.

The thickness of the matrix may be adjusted by the thickness of the gasket material used in the chamber. The shape of the chamber need not be rectangular, nor the resulting matrix planar. The chamber may also be a continuous surface of any shape, as in a bladder, sack, or other type of flexible container that may be selectively deformed to obtain the desired shape and thickness of the matrix with ports for introduction of matrix-forming solution and displacement of air. The surface of the chamber is also removable to expose a surface for freeze-drying.

The matrix-forming fluid contained in the chamber is frozen by the removal of heat at a controlled rate. This occurs predominantly through the two plates by simultaneous and symmetric application of a coolant to the opposite sides of the plates. Application of the coolant may be accomplished by several mechanisms. As one example, the sealed chamber containing the matrix-forming solution may be submerged or flooded with a chilled liquid coolant in an open bath of a static coolant. As another example, a coolant may be contained in a closed, recirculating system that flows in contact with the parallel plates of the chamber. As yet another example, a liquid or gaseous coolant may flow through an open vessel and be exhausted without recirculation. To establish a closed, recirculating coolant system, the plates between which the matrix-forming solution is placed and sealed may themselves be incorporated into a single apparatus, such as two containers through which the coolant flows (coolers). In one embodiment, the plates contacting the matrix-forming solution comprise one surface each of two hollow boxes with ports for supply and return vessels (i.e., tubing) of the coolant to a recirculating chiller, or for supply and exhaust of a flowing, non-recirculating coolant, such as liquid nitrogen.

The structure of any given formulation of matrix may then be regulated by controlling the rate of freezing. This may be accomplished in a number of ways, for example, by adjustment of the coolant temperature and volume in an open system; by adjustment of the coolant temperature and flow rate in a closed system; by selection of a coolant having a specific heat capacity; or by selection of the materials for the chamber and/or apparatus with preferred conductivities of heat. The structure of the matrix may also be regulated by the formulation of the matrix-forming solution.

The frozen matrix is subsequently dehydrated, crosslinked with or without the use of chemical crosslinking agents, and sterilized to provide a support or scaffold on which cells may be inoculated. The controlled and symmetric rate of freezing of the matrix produces uniform and symmetric reticulations throughout the uniform thickness of the matrix, which facilitate uniform cell distributions in the matrix and provide an enhanced surgical device.

Figure 1B:
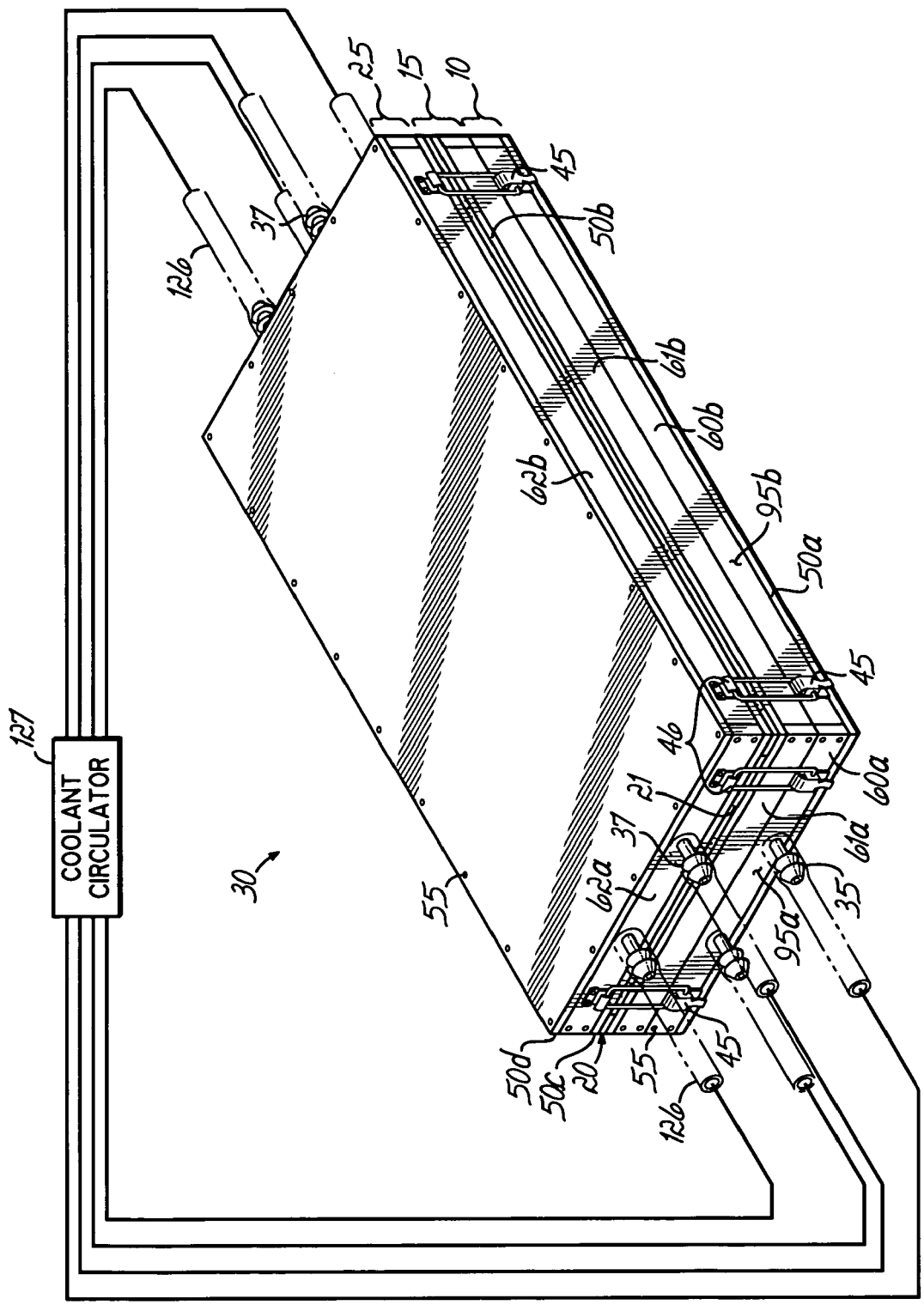
FIG. 1B shows the assembled apparatus.

In one embodiment, as shown in FIGS. 1A-B, the matrix-forming apparatus 30 consists of three frames that, upon assembly, form a preparation device or freezing apparatus. The three frames are a bottom frame 10, a center frame 15 which is also referred to as a carrier plate, and a top frame 25. Frames 10, 15, and 25 may be constructed of a metal, such as aluminum or steel, or another inflexible material such as wood, ceramic, or hard plastic. Apparatus 30 also includes a resilient spacer gasket 20, a spacer gasket plug 21, and "O" ring gaskets (not shown) which may be silicone rubber or other synthetic material.

Center frame 15 has a top surface 51$b$, and top frame 25 has a bottom surface 51$c$, both surfaces 51$b$, 51$c$ may be of any non-adherent material that resists deformation (for example, polished aluminum or other metal, ceramic, etc.) to facilitate removal of the of the subsequently formed matrix. Alternatively, a thin sheet 53 of a non-stick material such as TEFLON™ may be placed between spacer gasket 20 and top frame 25 to provide an additional non-adherent surface to facilitate separation of bottom surface 51$c$ from the frozen matrix. The surfaces 51$b$, 51$c$ may also be coated with a non-adherent material. Spacer gasket 20 and spacer gasket plug 21 may be made of a silicone rubber or other appropriate material.

Figure 1C:
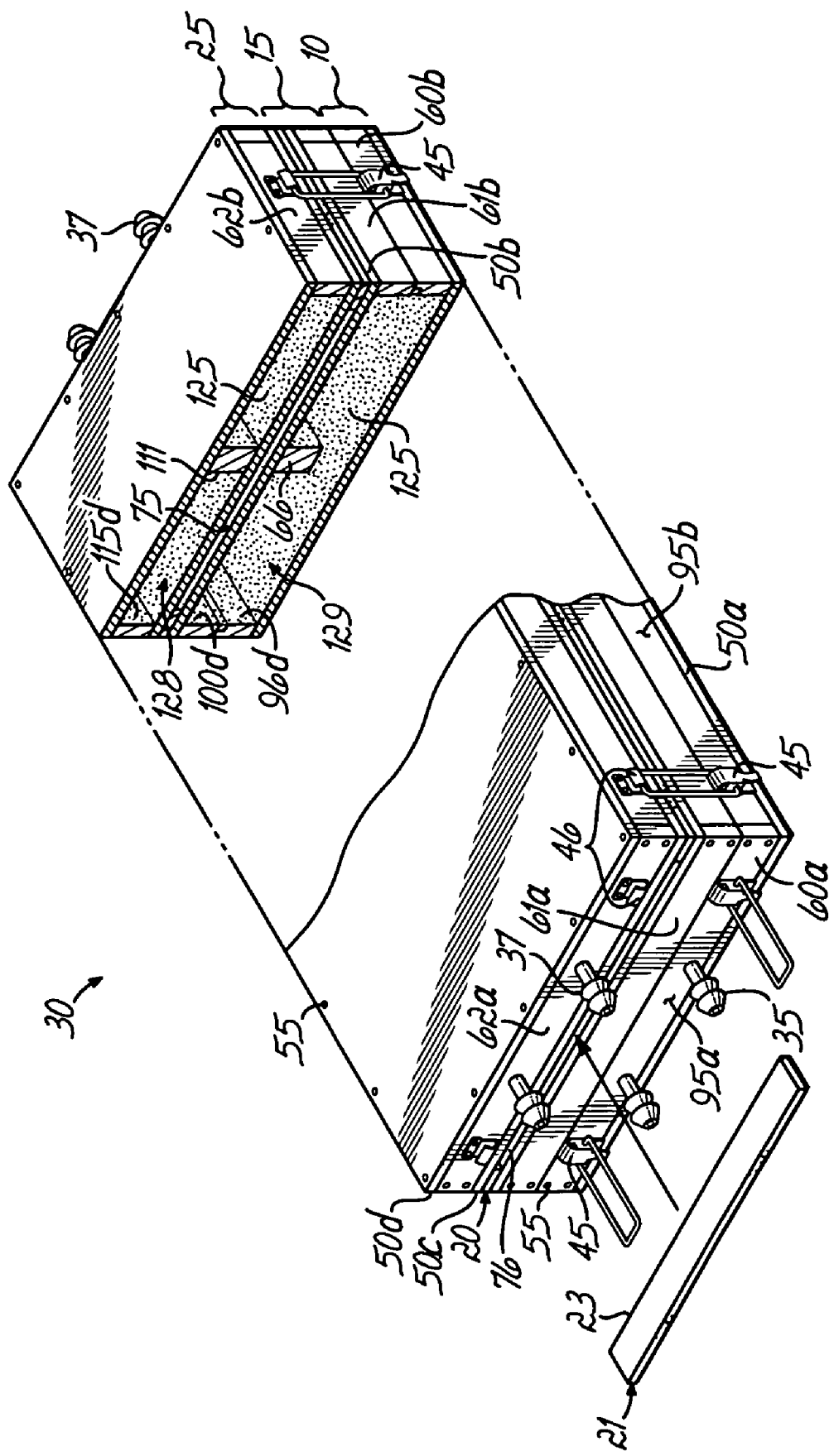
FIG. 1C is a cross-section view of the apparatus.
Figure 1D:
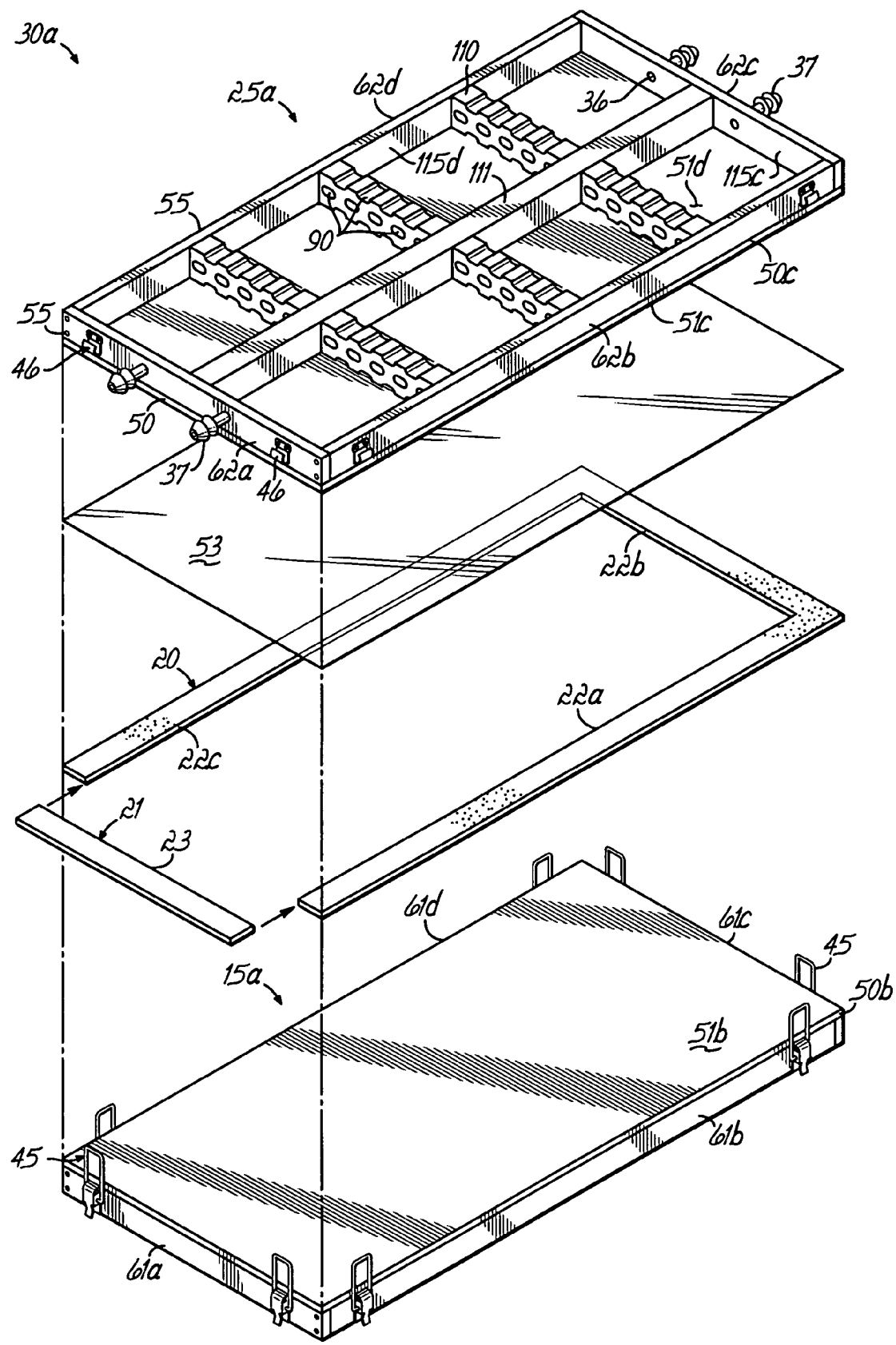
FIG. 1D shows the components of a second embodiment of the matrix-casting apparatus.
Figure 1E:
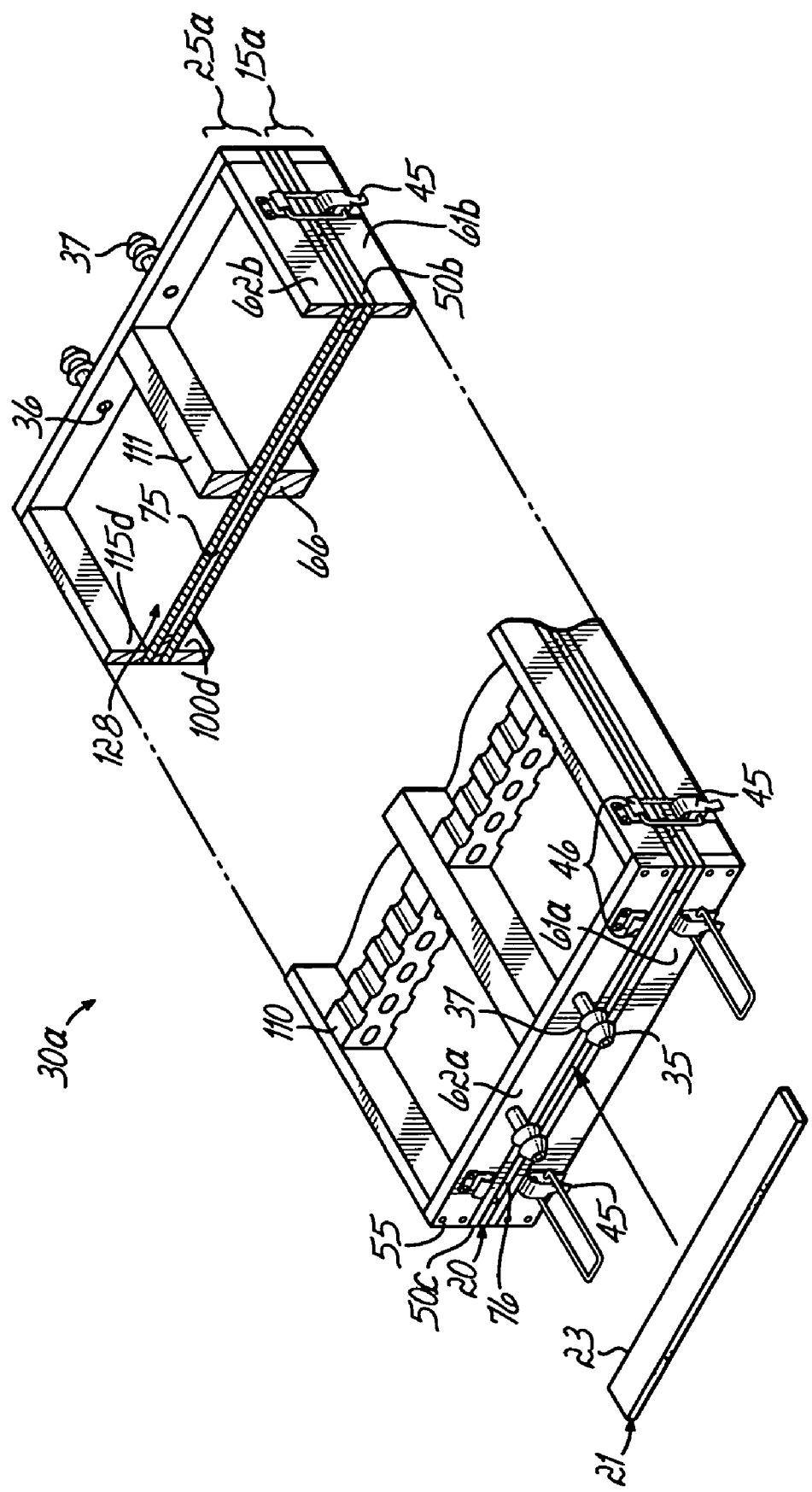
FIG. 1E is a cross-section view of the second embodiment of the matrix-casting apparatus

With reference to FIGS. 1D and 1E in which the reference numerals refer to like features in FIGS. 1A-1C the matrix-forming apparatus 30$a$ may optionally be used independent of the bottom frame 10 and top plate 50$d$ of apparatus 30. This embodiment is useful for exposure of the apparatus 30 containing the matrix-forming solution to a static coolant. This embodiment also includes a top frame 25$a$ without sheet 50$d$ so that the coolant may be in direct contact with surface 51$d$ of sheet 50$c$, a center frame 15$a$, also called a carrier plate, having a fastener such as a one half draw latch 45 adapted to the outside surfaces of the frame walls 61$a$-$d$, a spacer gasket 20, a spacer gasket plug 21, and optionally a non-stick sheet 53.

The frames 10, 15, 25 and gaskets 20, 21 are assembled to form the apparatus 30 by fastening the components together as shown in FIG. 1B. As shown in FIG. 1C within the assembled apparatus 30 is a chamber 75 capable of containing the matrix-forming fluid for subsequent controlled-rate freezing. The chamber 75 is defined by the following surfaces: the inner walls 22a-c of the spacer gasket 20, the inner wall 23 of the spacer gasket plug 21, the top surface 51b of the center frame 15 with or without the optional non-stick sheet 53, and the bottom surface 51c of the top frame 25. The spacer gasket 20 and spacer gasket plug 21 are of the same thickness, which regulates the thickness of the resulting matrix formed within the apparatus 30. In one embodiment, the gasket 20 and gasket plug 21 have a thickness in the range of about 0.1 mm to about 10 mm. In another embodiment, the gasket 20 and gasket plug 21 have a thickness in the range of about 0.5 mm to about 1.5 mm. Each of these components of the apparatus 30 will now be described in further detail.

Bottom Frame

Figure 2A:
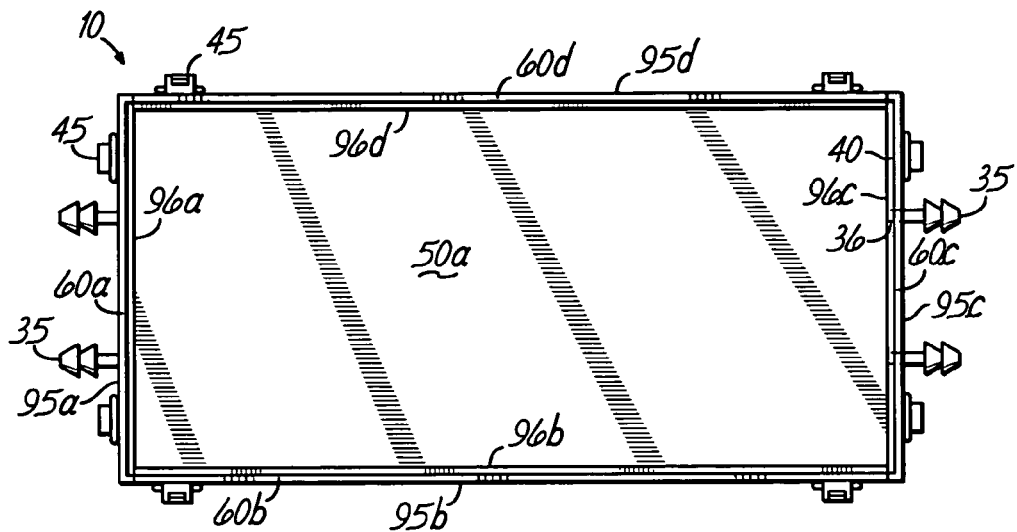
FIG. 2A is a top view of the bottom frame of the apparatus.
Figure 2B:
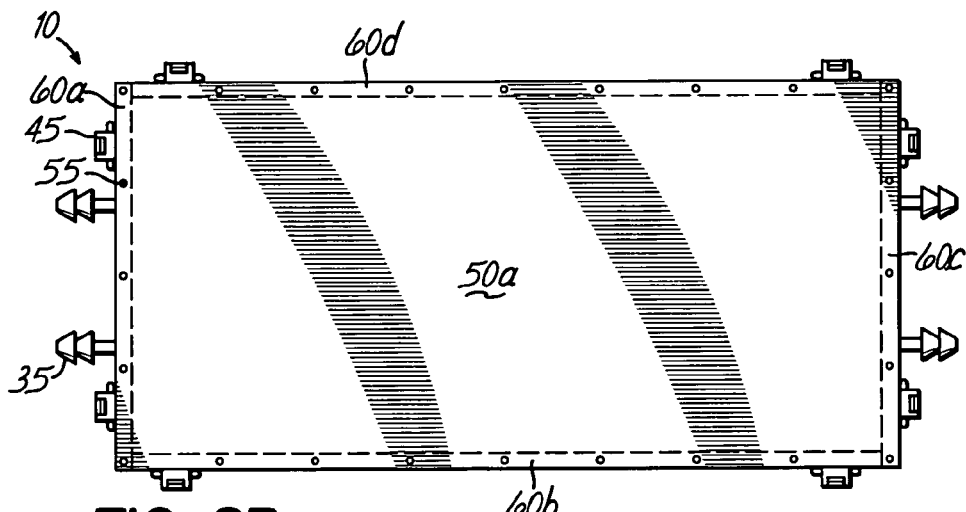
FIG. 2B is a bottom view of the bottom frame of the apparatus.
Figure 2C:
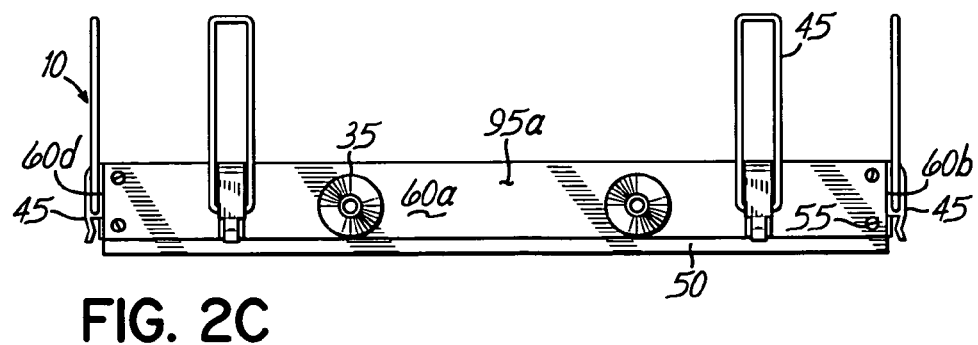
FIG. 2C is a side view of the bottom frame of the apparatus.

The components of the bottom frame 10 are shown in FIGS. 2A-C. The frame has at least four sides, or walls, 60a-d, and may be constructed of a metal, such as aluminum or steel, or another substantially or rigid material such as wood, ceramic, or hard plastic. The bottom frame 10 has a resilient gasket or O ring (not shown) which may be silicone, rubber, or other synthetic material. The O ring is affixed in the channel groove 40 that is recessed in the interior upper surfaces of the frame walls 60a-d. There is also a metal sheet 50a adapted to the bottom surfaces of the frame walls 60a-d; in one embodiment the sheet is made of aluminum. The edges of the frame walls 60a-d and the edges of the bottom metal sheet 50a may have holes (not shown) for receiving fasteners 55, as shown in FIGS. 2B-C, and/or fastening by welding, riveting, or using a metal adhesive to seal the joints of the respective frame walls. Alternatively, these parts may be permanently affixed, for example, the frame walls 60a-d may be constructed from a solid material such that there are no joints between the walls. The holes are aligned with corresponding holes in either the metal sheet 50a or frame walls 60a-d. At least two opposing frame walls 60a and 60c of the bottom frame 10 have at least one flow port 36 that allows flow along the entire width of the frame walls 60a, 60c extending from the outside vertical surfaces 95a, 95c to the inside vertical surfaces 96a, 96c of the frame walls 60a and 60c. Hose barbs 35 are adapted to flow ports 36. At least two opposing frame walls 60a and 60c, 60b and 60d, or both have fasteners 45 which are any type of couplers or other attachments to mate assembly 10 with the top assembly 25, such as with at least one half of a draw latch 45a adapted to their outer vertical surfaces 95a-d.

Center Frame

Figure 3A:
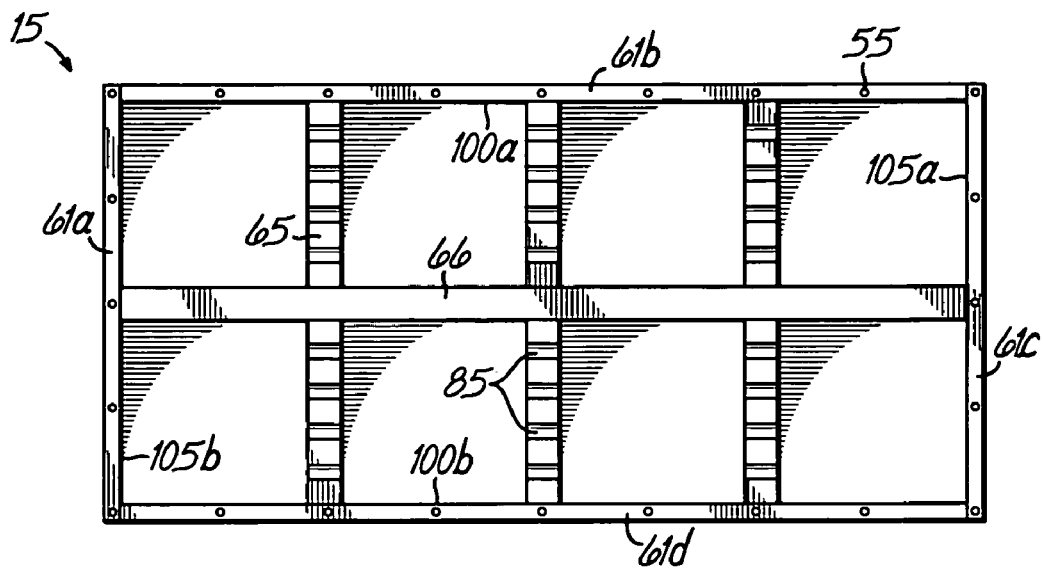
FIG. 3A is a bottom view of the center frame of the apparatus.
Figure 3B:
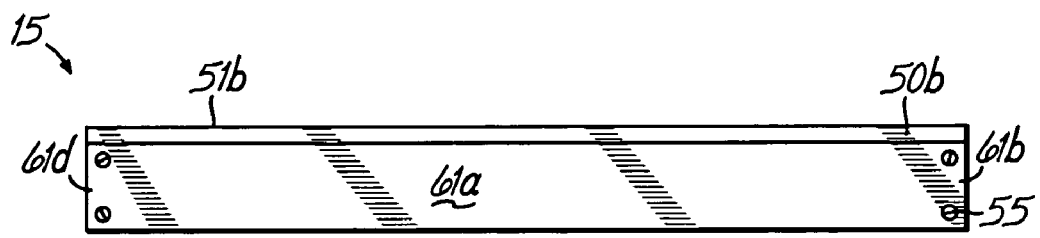
FIG. 3B is a side view of the center frame of the apparatus.
Figure 3C:
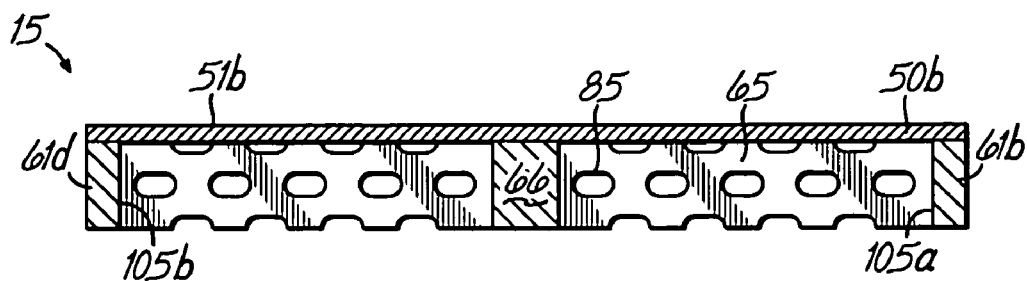
FIG. 3C is a cross section view of the center frame of the apparatus.

The center frame 15, or carrier plate, with various components is shown in FIGS. 1A, 3A, 3B, and 3C. As shown in FIGS. 3A and 3C, the frame 15 has at least one internal support 65 adapted to inner surfaces 100a and 100b of the frame walls 61b and 61d in the interior of the frame 15, and may have at least one internal frame support 66 adapted to the inner surfaces 105a and 105b of the frame walls 61a and 61c. Along its length, internal support 65 has a plurality of recessed flow vents 85 oriented in the direction of coolant flow to conduct coolant and allow coolant flow through the center frame 15. The walls of the center frame 15 are constructed of any material, and may be jointed or continuous, as previously described for the bottom frame 10.

The center frame 15 has a substantially rigid sheet 50b of a material, such as a metal or ceramic, that is adapted to the top surface (not shown) of the frame walls 61a-d. In one embodiment, sheet 50b has a mirrored-finished metal surface. The mirror-finished surface 51b of sheet 50b may also optionally be coated with a non-adherent material such as TEFLON™. The top surfaces of the frame walls 61a-d are adapted to a surface of sheet 50b using, for example, a metal adhesive, weld, or rivet.

Top Frame

Figure 4A:
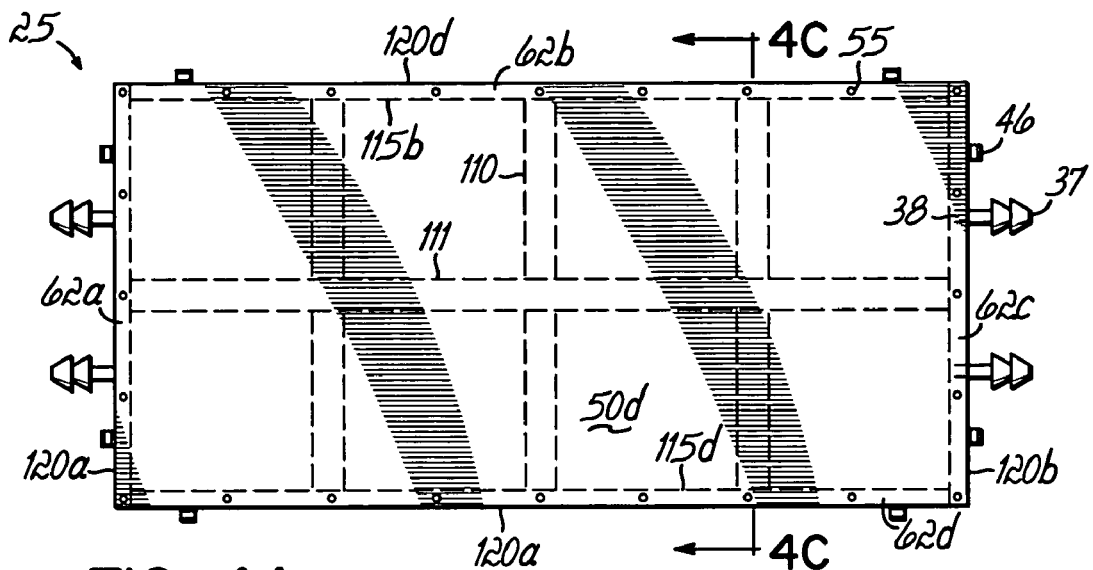
FIG. 4A is a top view of the top frame of the apparatus.
Figure 4B:
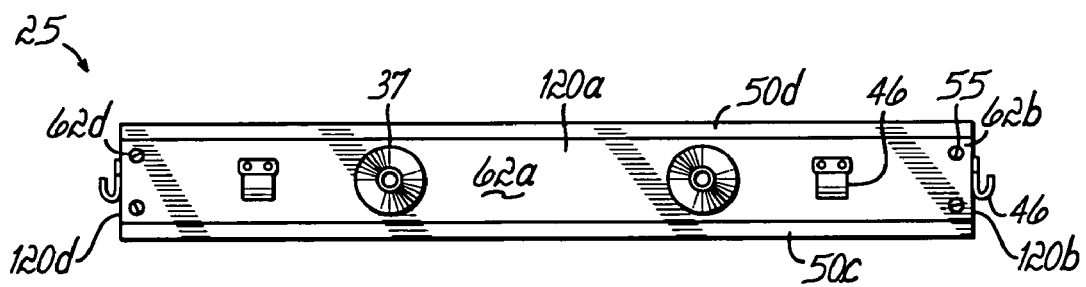
FIG. 4B is a side view of the top frame of the apparatus.
Figure 4C:
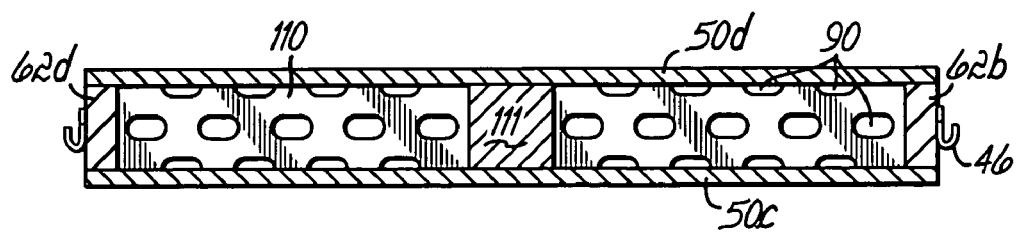
FIG. 4C is a cross section view of the top frame of the apparatus.

With reference to FIG. 4A, top frame 25 has four walls 62a-d, at least one support 110 connecting the interior surfaces 115b and 115d of walls 62b and 62d, and may have at least one internal support 111 connecting the interior surfaces 115a and 115c of walls 62a and 62c. The assembly, construction, and composition of walls and supports of the top frame 25 are as previously described for bottom frame 10. Internal support 110 has a plurality of recessed flow vents 90 that extend the entire width of the support 110 and are oriented in the direction of coolant flow. At least two opposing frame walls, for example 62a and 62c, 62b and 62d, or both have at least one flow port 38 that extends the entire width of the frame walls 62a, 62c and hose barbs 37 adapted to the flow ports 38. At least two opposing frame walls 62a and 62c, 62b and 62d, or both have couples, fasteners, or attachments 46 such as a draw latch adapted to outer vertical surfaces 120a-d of the top frame walls 62a-62d. The couplers, fasteners, or attachments 45, 46 are mated to secure the center frame 15 between the top frame 25 and bottom frame 10. Previously described surfaces 51c and 51d are adapted to the top and bottom surfaces of the frame walls 62a-d, both of which have holes (not shown) for receiving fasteners 55 which are aligned with corresponding holes in a frame wall or a sheet, and forms a coolant chamber 128 for receiving coolant 125 as shown in FIG. 1C.

Apparatus Assembly and Matrix Formation

Referring to FIGS. 1A, 1B, and 1C to assemble the apparatus 30 a resilient material (for example, a gasket) or member (for example, an O ring) (not shown) to make a fluid-tight joint, is placed in the channel groove 40 of the bottom frame 10. The center frame 15 is placed on top of the bottom frame 10, with the resilient gasket or O ring forming a seal between center frame 15 and bottom frame 10, thus forming a coolant chamber 129 for receiving coolant 125. A spacer gasket 20 is placed on the top surface 51b of the metal sheet 50b, such that a portion of the spacer gasket 20 is flush with three of the outer edges of the center frame 15. Optionally, an additional sheet 53 of a non-adherent material (i.e., TEFLON™) is overlaid on the spacer gasket 20, with the edges of the sheet 53 extending to the outer edges of the spacer gasket 20. The top frame 25 is then placed over the spacer gasket 20 so that the bottom surface 51c of frame 25 is in contact with either the spacer gasket 20 or the optional sheet 53. The frames 10, 15, 25 are fastened together, for example, by securing half drawn latches 45 and 46 to each other.

As illustrated in FIG. 1C, a chamber 75, to contain a matrix-forming fluid defined by the interior surfaces 22a-c of spacer gasket 20, the bottom optional surface 51c of sheet 50c of top frame 25, or a surface of the optional sheet 53, and the top surface 51b of sheet 50b of center frame 15. The chamber 75 has an opening 76 on one side to introduce the matrix-forming fluid and to insert the spacer gasket plug 21. The inner surface 23 of the spacer gasket plug 21 forms a wall of the chamber 75 when the spacer gasket plug 21 is inserted into the chamber opening 76.

The matrix-forming fluid is introduced into the chamber 75 of the apparatus 30, either through opening 76 or by another means, substantially filling the entire chamber 75. In one embodiment, the fluid is introduced incrementally, for example, in increments of about 20 ml-30 ml, with intermittent tapping of the apparatus 30 to avoid trapping bubbles in the fluid. Spacer plug 21 is then inserted into the opening 76 to seal the chamber 75, thus containing the matrix-forming fluid. The matrix-forming fluid contained within chamber 75 is then cooled at a controlled rate to solidify the matrix-forming fluid and thereby form the matrix.

As illustrated in FIG. 1B, the apparatus 30 is cooled by indirect contact of the chamber 75 with a source of coolant 125, via a conduit such as a hose 126 or other type of tubing connected to hose barbs 35 and 37. The conduit 126 may be connected to a coolant circulator 127 for recirculating flow of coolant 125. Alternatively, the coolant 125 may exhaust. In either case, coolant 125 flows directionally within the walls 60a-d of the bottom frame 10 and the walls 61a-d of the center frame 15 which are fastened together, and within the walls 62a-d of the top frame 25, for a time and at a flow rate and temperature sufficient to effect controlled freezing of the matrix.

Use of a system that flows or recirculates coolant 125 is advantageous for several reasons. The system is closed, and hence is less hazardous and more contained than an open system, such as a static controlled-temperature bath. The system prevents loss of the coolant 125, and allows a coolant-containing reservoir of any volume to be used. The system maintains a more stable temperature and, therefore, generates a more stable rate of cooling. Control of the rate of cooling is a factor in the determination of the distribution of reticulations of the polymer that forms the matrix. A stable controlled rate of cooling results in matrices having a reproducibly consistent and desirable distribution and quality of reticulations.

While the chamber 75 of apparatus 30 has six surfaces which are identified by numerals 22a-c, 23, 51b, and 51c (the boundaries of the "box"), four of these surfaces, defined by numerals 22a-c and 23, are insulated by the gaskets 20, 21 between the surfaces of sheets 50b and 50c. Therefore, virtually all of the heat is removed, and the cooling is regulated, through these two surfaces of sheets 50b and 50c. In this respect, the cooling of the matrix-forming fluid could be referred to as occurring between the two surfaces 51b and 51c.

Any type of fluid coolant 125 that is able to absorb heat and to lower the temperature in the chamber 75 sufficient to freeze the matrix-containing fluid at a controlled rate, that is, to effect a decrease in temperature from about 4° C. to about −70° C. in less than about two hours, for example, from about ten minutes to about twenty minutes, or less than about one-half hour. Fluid cooling advantageously occurs with efficiency and predictability, and furthermore is more easily regulated than air cooling, in the same manner as fluid cooling of an automobile engine occurs more efficiently than does air cooling. Examples of coolants which may be used include, but are not limited to, alcohols (for example, ethanol, propanol, etc.), polyethylene glycol, oils, silicone oils, or any fluid with low viscosity at temperatures down to −70° C., etc. In one embodiment, the temperature of the coolant is between about 0° C. and about −200° C. In another embodiment, the temperature of the coolant is between about −20° C. and −70° C. In yet another embodiment, the temperature of the coolant is between about −40° C. and −70° C. These temperatures regulate the average size and distribution of the reticulations in the matrix. As one example, the matrix-forming fluid is exposed to 95% ethanol that has been chilled to −45° C. for between 60 minutes and 120 minutes. Other embodiments are also within the knowledge of one skilled in the art.

Gases that have a vapor transition temperature which permit freezing of the matrix-forming solution can also be used as a coolant, as known to one skilled in the art. For example, gaseous nitrogen (vapor transition temperature −196° C.), known to one skilled in the art to effect controlled rate freezing of cells in culture, is sufficiently cold to freeze the matrix-forming fluid. In embodiments using a gas coolant, the flow of gas may be increased to compensate for the decreased efficiency of cooling with a gas, compared to a liquid which can absorb more heat. Increased flow of a gas may be easier to achieve than with a liquid because a pump would not be required. Other advantages of using a gaseous coolant are that small leaks would not be problematic, as they may be with liquid cooling, and a gas coolant system would be cleaner because there would be no attendant liquid spills.

For static cooling, the embodiment of the apparatus 30a illustrated in FIGS. 1D and 1E is used. The chamber 75 is configured without the bottom frame 10 and without the sheet 50d of the top frame 25. The chamber 75 is sealed at the perimeter 22a-c and 23 to prevent contact between the matrix-forming solution and the liquid coolant, because contact would result in failure to freeze or melting of the matrix. Alternatively, the chamber 75 within apparatus 30a is sealed at only three of the four sides (for example, 22a-c), leaving the fourth side unsealed. The apparatus 30a is then immersed or dipped into a bath of fluid coolant up to, but not over, the unsealed side.

After exposing the matrix-forming solution to a coolant under conditions sufficient to freeze the solution and form a matrix, the closures 45 are released. The top frame 25 is carefully removed from the center frame 15, upon which the matrix is supported on the surface 51b of sheet 50b. The non-stick sheet 53, if present, is removed carefully from the top surface of the frozen matrix. The spacer gasket 20 and spacer gasket plug 21 may optionally be removed from the center frame 15 and the matrix. The center frame 15 is removed from the bottom frame 10. The center frame 15, supporting the matrix 130 on surface 51b of sheet 50b, is placed in a freeze-drying device to lyophilize the ice from the matrix 130.

The rate of freezing of the matrix-forming fluid may be controlled by adjustment of one or more variables that contribute to the rapid heat transfer from the matrix-forming solution to the ambient environment. Therefore, the invention includes use of an apparatus 30 or 30a, to contain and contact the matrix-forming fluid, made of a material which allows highly efficient heat transfer. The apparatus 30 itself allows regulation of several variables during the freezing process. These variables include the shape and dimensions of the apparatus 30, the volume of matrix-forming fluid that is contained, and the thermal conductivity and specific heat of the materials which contact the matrix-forming fluid, that is, the specific material forming the substantially rigid and flat sheets 50b and 50c which contact the matrix-forming fluid. One example of such a material is metal (for example, aluminum, stainless steel, etc) which is a good conductor of heat. Desirably, the material is also substantially rigid to resist deformation, and contains a nonstick and/or polished surface that is in contact with the matrix-forming fluid.

The size and uniformity of the reticulations in the matrix formed from the matrix-forming fluid result from the size of ice crystals formed during the freezing process, because the ice displaces the solute in the fluid and thus determines the distance between reticulations. The size of ice crystals is inversely proportional to the rate of freezing. The rate of freezing is inversely proportional to the temperature of the coolant, and directly proportional to the thermal conductivity and specific heat of any materials which contact the matrix-forming fluid during the freezing process.

The size and distribution of the reticulations in the matrix may also be regulated by the temperature at which the components in the matrix-forming fluid freeze. The distance between the reticulations is inversely proportional to the concentration of components and to the rate of freezing of the matrix-forming fluid, and directly proportional to the concentration of water in the matrix-forming fluid. The thickness of the matrix is directly proportional to the concentration of components in the matrix-forming fluid. The concentrations of components in the matrix-forming fluid may be formulated to yield a combined % wt/vol concentration which decreases the average distance between the reticulations, and increases the thickness of the matrix. In one embodiment, combined component concentrations in the range of about $0.10\%^{wt/vol}$ to about $2.0\%^{wt/vol}$ matrix compounds may be used. In another embodiment, combined component concentrations in the range of about $0.50\%^{wt/vol}$ to about $1.80\%^{wt/vol}$ may be used. The thickness of the matrix is also is directly proportional to the thickness of the spacer gasket 20 and spacer gasket plug 21 used in the chamber 75. In one embodiment, the chamber 75 is configured to result in a matrix having a thickness is in the range of about 0.1 mm to about 3.0 mm.

The responses to the freezing temperature of the size and distribution of the reticulations prepared using the inventive method and apparatus may be determined by measurement of scanning electron micrographs (SEM) of the rehydrated and dried matrix. In one embodiment, the reticulations are distributed in the shape of ellipsoid spheres and have an average diameter in the range of about 50 μm to about 150 μm.

An apparatus 30 for preparing a biocompatible matrix, and a method of using the apparatus 30 to prepare a biocompatible matrix, are thus disclosed. The inventive apparatus 30 and method provide a matrix capable of supporting cells to form an implantable or engraftable surgical device, such as a cultured skin device for temporary or permanent skin replacement on a burn or other wound. The matrix is used to support one or more layers of cultured dermal cells, which serve as a lamination layer for a epidermal cells. Other variations or embodiments of the invention will also be apparent to one of ordinary skill in the art from the above description. Thus, the forgoing embodiments are not to be construed as limiting the scope of this invention.

What is claimed is:

1. A biocompatible matrix, said matrix prepared by
providing a matrix-forming fluid to an apparatus wherein the fluid is contained between a first thermally conductive surface and a second thermally conductive surface and has substantially uniform thickness,
cooling the fluid at a controlled rate to simultaneously remove heat from said first and second surfaces to form a frozen matrix by circulating a coolant fluid within a coolant chamber containing the apparatus,
dehydrating the solid sheet to form the matrix, and
physically crosslinking the matrix to result in a biocompatible matrix.

2. The matrix of claim 1 capable of supporting at least one cell type inoculated thereon, the cell type selected from the group consisting of epidermal cells, dermal cells and combinations thereof.

3. The matrix of claim 1 wherein the fluid contains a substance selected from the group consisting of a carbohydrate, a protein, a polypeptide, and combinations thereof.

4. The matrix of claim 1 wherein cooling is at a rate to effect a decrease in temperature from about 4° C. to about −70° C. at a time up to about two hours.

5. The matrix of claim 1 wherein at least one of the thermally conductive surfaces is substantially non-adherent to the matrix.

6. The matrix of claim 1 wherein the thermally conductive material is a metal.

7. The matrix of claim 1 wherein said biocompatible matrix includes reticulations that are substantially uniform across the thickness of the matrix.

8. A biocompatible matrix including reticulations, the matrix prepared by
providing a matrix-forming fluid to an apparatus wherein the fluid is contained between a first thermally conductive surface and a second thermally conductive surface and has substantially uniform thickness,
cooling the fluid at a controlled rate to simultaneously remove heat from the first and second surfaces to form a frozen matrix,
dehydrating the solid sheet to form the matrix, and
physically crosslinking the matrix to result in a biocompatible matrix including reticulations.

9. The matrix of claim 8 capable of supporting at least one cell type inoculated thereon, the cell type selected from the group consisting of epidermal cells, dermal cells and combinations thereof.

10. The matrix of claim 8 wherein the fluid contains a substance selected from the group consisting of a carbohydrate, a protein, a polypeptide, and combinations thereof.

11. The matrix of claim 8 wherein cooling is at a rate to effect a decrease in temperature from about 4° C. to about −70° C. at a time up to about two hours.

12. The matrix of claim 8 wherein at least one of the thermally conductive surfaces is substantially non-adherent to the matrix.

13. The matrix of claim 8 wherein cooling is by circulating a coolant fluid within a coolant chamber containing the apparatus.

14. A biocompatible matrix including symmetric reticulations, the matrix prepared by
providing a matrix-forming fluid to an apparatus wherein the fluid is contained between a first thermally conductive surface and a second thermally conductive surface and has substantially uniform thickness,
cooling the fluid at a controlled rate to simultaneously remove heat from the first and second surfaces to form a frozen matrix,
dehydrating the solid sheet to form the matrix, and
physically crosslinking the matrix to result in a biocompatible matrix including symmetric reticulations.

15. The matrix of claim 14 capable of supporting at least one cell type inoculated thereon, the cell type selected from the group consisting of epidermal cells, dermal cells and combinations thereof.

16. The matrix of claim 14 wherein the fluid contains a substance selected from the group consisting of a carbohydrate, a protein, a polypeptide, and combinations thereof.

17. The matrix of claim 14 wherein cooling is at a rate to effect a decrease in temperature from about 4°C. to about −70° C. at a time up to about two hours.

18. The matrix of claim 14 wherein at least one of the thermally conductive surfaces is substantially non-adherent to the matrix.

19. The matrix of claim 14 wherein cooling is by circulating a coolant fluid within a coolant chamber containing the apparatus.

* * * * *

UNITED STATES PATENT AND TRADEMARK OFFICE
CERTIFICATE OF CORRECTION

| | | |
|---|---|---|
| PATENT NO. | : 7,452,720 B2 | Page 1 of 1 |
| APPLICATION NO. | : 11/142950 | |
| DATED | : November 18, 2008 | |
| INVENTOR(S) | : Steven T. Boyce | |

It is certified that error appears in the above-identified patent and that said Letters Patent is hereby corrected as shown below:

Column 1, line 5

After RELATED APPLICATIONS, please insert the following:

--This invention was made with government support under grants GM050509 awarded by the National Institute for General Medical Sciences, and FD-R-000672 awarded by the U.S. Food and Drug Administration Office of Orphan Products Development. The government has certain rights in the invention.--

Signed and Sealed this

Thirteenth Day of July, 2010

David J. Kappos
*Director of the United States Patent and Trademark Office*